United States Patent [19]
Selby et al.

[11] Patent Number: 5,993,628
[45] Date of Patent: Nov. 30, 1999

[54] ELECTROPHORESIS METHOD AND APPARATUS FOR SEPARATING BIO-ORGANIC MOLECULES

[75] Inventors: Barton G. Selby, San Carlos; Johan Goudberg; Binh Vo, both of San Jose; David Clark, Hayward, all of Calif.

[73] Assignee: The Perkin-Elmer Corporation, Foster City, Calif.

[21] Appl. No.: 09/062,381

[22] Filed: Apr. 17, 1998

[51] Int. Cl.[6] .......................... G01N 27/26; G01N 27/447
[52] U.S. Cl. .......................... 204/470; 204/466; 204/467; 204/616; 204/618; 204/620; 204/621
[58] Field of Search ...................... 204/618, 621, 204/620, 619, 616, 606, 456, 466, 467, 470

[56] References Cited

U.S. PATENT DOCUMENTS

| | | | |
|---|---|---|---|
| 4,663,015 | 5/1987 | Sleeter et al. ............................ | 204/618 |
| 4,915,811 | 4/1990 | Yamamoto et al. ..................... | 204/619 |
| 5,073,246 | 12/1991 | Chu et al. ................................ | 204/619 |
| 5,164,065 | 11/1992 | Bettencourt et al. ................... | 204/619 |
| 5,284,565 | 2/1994 | Chu et al. ................................ | 204/619 |
| 5,324,412 | 6/1994 | Kolner .................................... | 204/619 |
| 5,472,589 | 12/1995 | Jacobs ..................................... | 204/616 |
| 5,627,022 | 5/1997 | Renfrew et al. ..................... | 204/606 X |
| 5,656,145 | 8/1997 | Nguyen et al. ......................... | 204/618 |

FOREIGN PATENT DOCUMENTS

| | | |
|---|---|---|
| 0 285 394 | 10/1988 | European Pat. Off. . |
| 0 735 365 | 10/1996 | European Pat. Off. . |
| 0 735 365 A2 | 10/1996 | European Pat. Off. . |
| 63-47648 | 2/1988 | Japan .................................. 204/620 |
| 97 43630 | 11/1997 | WIPO . |

OTHER PUBLICATIONS

"96–Lane Upgrade," PE Applied Biosystems, *Online*! 1998. No month available.
International Search Report from related PCT Application No. PCT/US99/08351.
Kolner, D.E.., et al., "Ultrathin DNA Sequencing Gels Using Microtrough Vertical Electrophoresis Plates," Biotechniques 13(3):338–339 (1992).

*Primary Examiner*—Jill Warden
*Assistant Examiner*—John S. Starsiak, Jr.
*Attorney, Agent, or Firm*—Jeffrey D. Frazier

[57] ABSTRACT

The present invention relates to the electrophoretic separation of bio-organic molecules using a slab gel electrophoresis apparatus having a pair of spaced, confronting plates defining a multi-lane separation zone adapted to hold a separation medium and an upper loading zone. In one aspect of the invention, at least one of the plates is shaped to provide an expanded loading zone. The plate-to-plate distance within the expanded loading zone is greater than the plate-to-plate width within the separation zone. In another aspect of the invention, a comb is provided with each tooth having a gradual taper beginning at a support member and extending along most of the tooth's longitudinal axis, and a sharp taper beginning immediately beyond the gradual taper and extending to the end of the tooth. In a related aspect of the invention, a method is provided wherein a comb is inserted into the loading zone so that the teeth penetrate an upper portion of the separation medium, thereby forming a series of fluid-tight, elongate sample-loading apertures of substantially rectangular cross-section having a plate-to-plate width greater than that of the inter-plate distance in the separation zone.

18 Claims, 3 Drawing Sheets

ELECTROPHORESIS METHOD AND APPARATUS FOR SEPARATING BIO-ORGANIC MOLECULES

FIELD OF THE INVENTION

The present invention relates to the electrophoretic separation of analytes of interest, such as bio-organic molecules. In particular, the invention provides an improved slab gel electrophoresis apparatus, and method of use, for electrophoresis of samples using ultra-thin gels.

BACKGROUND OF THE INVENTION

Electrophoresis is a popular method for separating large molecules, such as DNA fragments or proteins, from a mixture of similar molecules. Generally, the method involves passing an electric current through a porous medium containing the mixture. Each kind of molecule travels through the medium at a different rate, depending on its electrical charge and size. This movement produces a series of bands in the medium. Each band corresponds to a molecule or fragment of a particular size, progressively decreasing down the gel. Agarose and acrylamide gels are media commonly used for electrophoresis of proteins and nucleic acids.

Due in large part to its usefulness in nucleic acid sequencing, slab gel electrophoresis has become increasingly important in the field of biotechnology. A slab gel apparatus is typically prepared by disposing two glass plates face-to-face, with spacers interposed at both vertical edges to establish a gap therebetween. In one approach, the plates are clamped together along the vertical edges and a seal is placed along the top or bottom edge. The gap between the plates is then filled with gel solution, and the gel is allowed to set. Next, the top and bottom of the polymerized gel are placed in contact with respective buffer reservoirs. Samples are loaded into sample loading slots at one end of the gel, and an electric field is set up across the gel. The electric field causes the molecules to move from the loading slots into the gel and to separate according to size.

Slab gels of very thin cross-section, in the direction perpendicular to the plane of electrophoresis, are particularly popular for nucleic acid sequencing thanks to a number of advantages they offer over thicker gels. For example, ultra-thin slab gels (e.g., 0.1 mm to 0.3 mm thick) can be electrophoresed at a higher voltage than traditional, thicker gels because of more efficient heat dissipation, thereby permitting a faster electrophoretic run. Ultra-thin gels also offer the advantage of higher resolution, because less sample is required and there is less time for diffusion during electrophoresis. Additionally, owing to their thinness, ultra-thin gels can be fixed for autoradiography with relative quickness and ease.

In using ultra-thin gels, it is desirable to increase lane density to achieve higher sample throughput. The dimensions of the sample lanes in the separation medium will typically depend on the dimensions of the regions into which the samples are loaded, the spacing between sample loading regions, the duration of time needed to transport the samples into the separation medium, and the level of diffusion during electrophoresis, for example.

Two types of sample-holding slots, known as "wells," are generally used in slab gels. In one approach, the wells are molded directly into the gel material using a template. The template, known as a comb, comprises a plurality of square-ended, evenly spaced protrusions extending off one edge of an elongate support member. To form the wells, the protrusions of the comb are inserted into the top of a gel solution before it has polymerized. The gel is then allowed to solidify. After the template is removed from the polymerized gel, empty wells remain for receiving samples. In such a construction, the loaded samples are separated from each other by finger-like extensions of the polymerized gel. In the other common type of well, often used with ultra-thin gels, sample-holding slots are created by inserting narrow, wedge-shaped, pointed protrusions of a "shark's tooth" comb partially into the top of the gel after it has polymerized. Samples are loaded into empty spaces bounded by adjacent teeth of the comb and the inner surfaces of the glass plates. The teeth of the shark's tooth comb, thus, serve as barriers to prevent the mixing of adjacent samples.

In most slab gel setups, the thickness of each well is determined by the thickness of the gel. Consequently, ultra-thin gels typically have ultra-thin sample wells. As a practical matter, it is difficult to load gels having wells that have a thickness of 0.2 mm or less. In this regard, sample loading is usually attempted by inserting a loader tube, such as a flat pipette tip or tapered glass capillary, having an extremely small outer diameter, between the two plates to deposit samples into the wells. To prevent sample mixing, it is desirable to inject the sample as close to the gel as possible. Under circumstances where the wells are very thin and the lane density is high, however, it can be very difficult to maneuver the tip of the loading implement between the plates and into position proximate the gel. Moreover, the loader tubes themselves can present additional problems. For example, viscous samples can be difficult to deposit with such small loading devices because their narrow bores easily clog and the tapered tips readily break. Also, loader tubes having ultra-small tips can be expensive and difficult to obtain.

As previously discussed, two types of templates, or combs, have traditionally been used for forming sample-loading slots; namely, square-tooth combs and shark's tooth combs. Although satisfactory in certain respects, each type of comb nevertheless presents certain problems.

Often, the bottom of a well formed with a square-tooth comb will have an uneven surface. This can be caused, for example, by unpolymerized gel material remaining in the well and/or by tearing of the gel upon withdrawal of the comb. An uneven gel surface, in turn, can result in crooked bands and/or skewed lanes during electrophoresis.

The projections, or teeth, of a shark's tooth comb tend to be very thin and flexible. This is especially true of combs having a large number of teeth (e.g., 48 teeth or higher). Upon pressing a comb into a polymerized gel, the teeth encounter a slight amount of resistance. Unfortunately, thin teeth sometimes bend as a result of such resistance. Bent teeth can distort the gel, resulting in crooked bands and/or skewed lanes during electrophoresis. Bent teeth can also change the volume between adjacent teeth for accommodating sample. Thus, maximum sample volumes can vary from well to well. Moreover, thin, flexible teeth have also been associated with cross-leakage of samples. Thin teeth also tend to be weak and prone to breakage.

Generally, the teeth of shark's tooth combs are especially thin towards their outer ends, in the region whereat the interface of the well and the gel is defined. For this reason, the barrier between adjacent wells is often not very substantial. Upon electrophoresis, the lanes run very close to one another. That is, there is insufficient separation, or "dark space", between lanes. As a result, it is sometimes difficult to distinguish the border between adjacent lanes. This can cause misreads by automated sequencing equipment. For example, the reader might interpret two adjacent bands, representing molecules of a particular length or molecular weight, as a single band. Consequently, the reader would report only one band, which it would assign to only one of the two adjacent lanes. Thus, the closely spaced band in the adjacent lane would go unreported. Of course, lane drifting can further complicate this problem, especially where lanes actually converge into one another.

In an effort to accommodate a large number of wells on a single gel, some shark's tooth comb designs have the teeth spaced very close together. With such combs, the apertures between adjacent teeth do not provide much space for accommodating sample. This is particularly true with combs designed for conventional ultra-thin slab gel setups. So, the user is restricted to using only very small sample volumes (e.g., less than 1 microliter).

The widespread use of 96-well trays in the field of biotechnology makes the use of a 96-well, slab gel electrophoresis apparatus especially attractive. For example, a single sequencing run could match the contents of a 96-well thermocylcer plate. The known slab gel setups, however, are not able to complement 96-well trays in this manner. For practical purposes, the wells formed by conventional, square-ended combs are too large to fit 96 of them on a single slab gel. Regarding shark's tooth combs, problems associated with thin teeth, such as those discussed above, render these inadequate for creating 96 wells on a single slab gel.

In view of the foregoing, the need is apparent for a method and apparatus that realize the advantages offered by ultra-thin slab gel electrophoresis having high-lane density, while avoiding the deficiencies and problems associated with the prior setups.

SUMMARY OF THE INVENTION

The present invention provides, in one aspect, an improvement for a slab gel electrophoresis apparatus having a pair of spaced, confronting plates defining a multi-lane separation zone adapted to hold a separation medium and an elongate upper loading zone, and a comb having a plurality of teeth adapted to be inserted into the loading zone defining therewith a plurality of loading regions that communicate with the separation zone. The improvement includes an elongate recess formed in the upper portion of at least one plate. The recess forms, together with the confronting plate, an elongate upper loading zone having a plate-to-plate distance that (i) is substantially constant throughout the upper loading zone and (ii) is greater than the plate-to-plate distance within the separation zone. An elongate tapered portion joins the separation zone with the loading zone. The elongate tapered portion has a plate-to-plate distance that progressively decreases from the loading zone to the separation zone. A separation medium is held between the confronting plates within the separation zone and extends at least partially into the tapered portion.

In one embodiment, the separation medium held between the confronting plates extends from the separation zone at least partially into the loading zone.

The elongate recess preferably spans at least two adjacent loading regions formed by the comb. More preferably, the elongate recess spans at least 48 adjacent loading regions, and more preferably, spans at least 96 adjacent loading regions. In another embodiment, the elongate recess extends across at least 70%, and preferably at least 80% of the lateral width of one of the plates.

In a further embodiment, the plate-to-plate distance within the separation zone is less than 0.3 mm, and the plate-to-plate distance within the loading zone is greater than 0.3 mm. In a related embodiment, the plate-to-plate distance within the separation zone is about 0.2 mm. In another related embodiment, the plate-to-plate distance within the loading zone is from 1.5 to 3 times the plate-to-plate distance within the separation zone.

In another embodiment, the teeth of the comb extend off one edge of an elongate support member. In one embodiment, each tooth contains (i) a first region beginning proximal to and extending away from the support member, such that the first region is optionally tapered, and (ii) a terminal region that is more tapered than the first region and has a pointed end, for forming a liquid-tight seal with the top of the separation medium. In a more specific embodiment, each tooth has (i) a first tapered portion which tapers gradually beginning proximate to the support member and extending along most of the tooth's longitudinal axis, and (ii) a second tapered portion, more sharply tapered than the first tapered portion, which optionally begins immediately beyond the first tapered portion and extends along the tooth's longitudinal axis to an end of the tooth distal from the support member.

In a related embodiment, the teeth of the comb extend off one edge of an elongate support member and are positioned between the confronting plates in the loading zone with their distal end regions penetrating a surface of the separation medium. In this embodiment, the spacing between edges of adjacent teeth at their distal end regions where the teeth cross the surface of the separation medium is a multiple less than less than 3 times the width of the individual teeth where the teeth cross the surface of the separation medium.

Another aspect of the invention provides a comb for a slab gel electrophoresis apparatus having a pair of spaced, confronting plates defining a multi-lane separation zone adapted to hold a separation medium and an elongate upper loading zone, and a separation medium held within the separation zone. The comb includes an elongate support member and a series of teeth extending from one edge of the support member. The teeth are positioned between the confronting plates in the loading zone with their distal end regions penetrating a surface of the separation medium. The teeth and confronting plates define a plurality of loading regions, between adjacent teeth, that communicate with the separation zone. The spacing between adjacent teeth at their distal end regions where the teeth cross the surface of the separation medium is a multiple less than 3 of the width of the individual teeth.

In one embodiment, the spacing between edges of adjacent teeth at their distal end regions where the teeth cross the surface of the separation medium is less than 1.35 mm, and the width of each individual tooth where the teeth cross the surface of the separation medium is greater than 0.45 mm. In a related embodiment, the spacing between edges of adjacent teeth at their distal end regions where the teeth cross the surface of the separation medium is between 1.2–1.3 mm, and the width of each individual tooth where the teeth cross the surface of the separation medium is between 0.5–0.6 mm.

In another embodiment relating, at least one of the plates has an elongate recess across an upper portion thereof. The recess forms, together with the confronting plate, an elongate upper loading zone having a plate-to-plate distance that (i) is substantially constant throughout the upper loading zone and (ii) is greater than the plate-to-plate distance within the separation zone. The plate further includes an elongate tapered portion joining the separation zone with the loading zone. The elongate tapered portion has a plate-to-plate distance that progressively decreases from the loading zone to the separation zone. Further in this embodiment, the separation medium extends at least partially into the tapered portion.

A further aspect of the invention provides an improvement for a slab gel electrophoresis apparatus having a pair of spaced, confronting plates defining a multi-lane separation zone adapted to hold a separation medium and an elongate upper loading zone, and a separation medium held within the separation zone. The improvement includes a comb having an elongate support member and a series of teeth extending from one edge of the support member. In one embodiment, each tooth contains (i) a first portion beginning proximal to and extending away from the support member, such that the first region is optionally tapered, and (ii) a terminal portion that is more tapered than the first portion and has a pointed end, for forming a liquid-tight seal with the top of the separation medium. In a more specific embodiment, each tooth has (i) a first tapered portion which tapers gradually beginning proximate to the support member and extending along most of the tooth's longitudinal axis, and (ii) a second tapered portion, more sharply tapered than the first tapered portion, which optionally begins immediately beyond the first tapered portion and extends along the tooth's longitudinal axis to an end of the tooth distal from the support member. The teeth are positioned between the plates in the loading zone with the distal end of each tooth penetrating the separation medium, thereby forming a plurality of elongate loading regions, between adjacent teeth, that communicate with the separation zone.

In one embodiment, the teeth have front and rear surfaces that are substantially planar and parallel to one another.

In another embodiment, the separation medium within the separation zone is less than 0.3 mm thick, and the teeth of the comb are greater than 0.3 mm thick. In a related embodiment, the face-to-face thickness of the comb is 1.5–3 times greater than the plate-to-plate distance within the separation zone.

In a further embodiment, the comb contains at least 97 teeth for forming at least 96 sample loading regions.

In another embodiment, each loading region has substantially the shape of an inverted "U."

In an additional embodiment, at least one of the plates has an elongate recess formed in the upper portion thereof. The recess forms, together with the confronting plate, an elongate upper loading zone having a plate-to-plate distance which (i) is substantially constant throughout the upper loading zone and (ii) is greater than the plate-to-plate distance within the separation zone. The plate further includes an elongate tapered portion joining the separation zone with the loading zone. The elongate tapered portion has a plate-to-plate distance that progressively decreases from the loading zone to the separation zone. Further, the separation medium extends at least partially into the tapered portion.

Another aspect of the invention provides a comb for a slab gel electrophoresis apparatus having a pair of spaced, confronting plates defining a multi-lane separation zone adapted to hold a separation medium and an elongate upper loading zone, and a separation medium held within the separation zone. The comb includes an elongate support member and a series of teeth extending from one edge of the support member. The teeth are positioned between the confronting plates in the loading zone with their distal end regions penetrating a surface of the separation medium. The teeth and confronting plates define a plurality of loading regions, between adjacent teeth, that communicate with the separation zone. The teeth have front and rear surfaces that are substantially planar and parallel to one another. Further, the face-to-face thickness of the comb is a multiple of greater than 1.1, and preferably greater than 1.5, and more preferably greater than 2, times the plate-to-plate distance in the separation zone.

An additional aspect of the invention provides a method of preparing a slab gel electrophoresis apparatus for use in separating bio-organic molecules. The method includes the step of providing a pair of spaced, confronting plates defining a multi-lane separation zone and an upper loading zone, a separation medium held within the separation zone, and a comb having a plurality of teeth adapted to be inserted into the loading zone. The method also includes the step of inserting the comb into the loading zone so that distal ends of the teeth penetrate an upper portion of the separation medium, thereby forming a plurality of loading regions, between adjacent teeth, that communicate with the separation zone. In a preferred embodiment, the loading regions are of substantially rectangular longitudinal cross-section, and the plate-to-plate distance within the loading regions is greater than the plate-to-plate distance in the separation zone.

These and other features and advantages of the present invention will become clear from the following description.

BRIEF DESCRIPTION OF THE DRAWINGS

The structure and manner of operation of the invention, together with the further objects and advantages thereof, may best be understood by reference to the following description taken in conjunction with the accompanying drawings, in which identical reference numerals identify similar elements, and in which.

DETAILED DESCRIPTION OF THE INVENTION

One aspect of the present invention provides an improved apparatus for the electrophoretic separation of bio-organic molecules, particularly nucleic acids such as DNA, using an ultra-thin gel.

Figure 1:
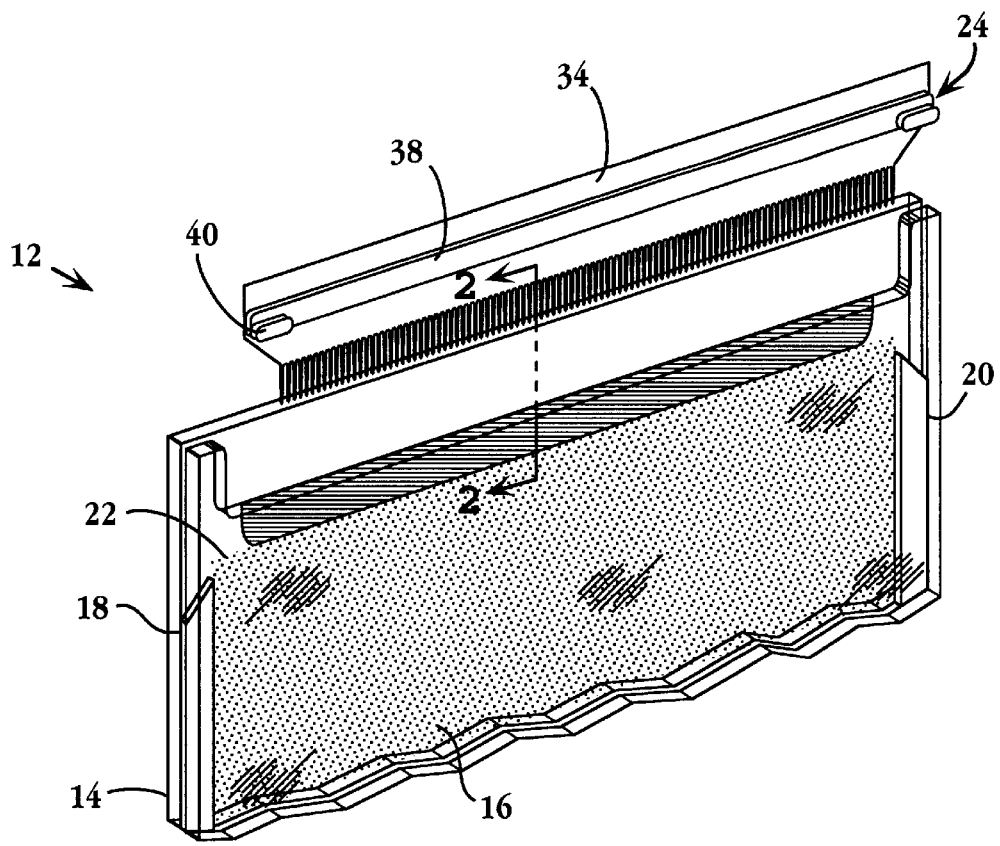
FIG. 1 is a perspective view of a slab gel electrophoresis apparatus, showing a pair of confronting plates separated by a pair of spacer strips and a comb poised above the plates, according to an embodiment of the present invention.

Referring in detail to the drawings, FIG. 1 is a perspective view of a slab gel electrophoresis apparatus, indicated generally by the reference numeral 12, constructed in accordance with the present invention. A pair of plates 14, 16 are disposed face-to-face with a pair of spacer strips 18, 20 interposed at both vertical edges to establish a gap 22 between the plates. The plates 14, 16 are compressed together by any suitable means (not shown), which could include any of various types of clamps or clips along their lateral edges. A comb 24 is shown poised above the plates 14, 16 prior to insertion into the upper region of the gap 22.

Figure 2:
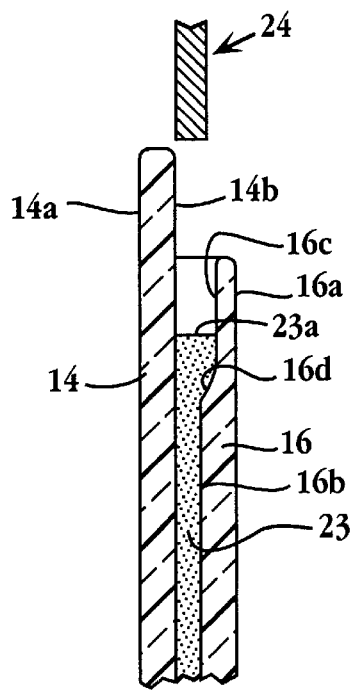
FIG. 2 is a side cross-sectional view taken along the line 2—2 of FIG. 1.

An electrophoresis medium layer, such as 23 shown in FIG. 2, is interposed between the two plates 14, 16 and occupies most of the gap 22. The electrophoresis medium layer 23 may be of any suitable type. For example, the electrophoresis medium layer 23 may comprise an agarose or acrylamide gel, optionally covalently crosslinked, and optionally containing a suitable denaturant such as urea. In a preferred embodiment, the electrophoresis medium layer 23 is formed of a 5% polyacrylamide gel.

Referring again to FIG. 1, the spacer strips 18, 20 establish the width of the gap 22 between the two plates 14, 16 and, hence, the width for the interposed gel. The spacer strips 18, 20 are formed of a non-conductive material capable of forming a watertight seal, such as polyester or MYLAR® (DuPont). The gap 22 defines a space that serves as both a mold cavity for the gel and the space to be occupied by the gel during electrophoresis. The space is bordered by confronting faces of the plates 14, 16 and the inner edges of the spacer strips 18, 20.

The cross-sectional view in FIG. 2 depicts additional details of the plates 14, 16. Plates 14 and 16 have inner faces, juxtaposed to one another, and outer faces which are directed away from one another. The outer and inner faces of plate 14, denoted respectively as 14a and 14b, and the outer face of plate 16, denoted as 16a, are all substantially planar and parallel to one another. The inner face of plate 16 has an elongate, shaped or recessed region, indicated in FIG. 1 by hatching, extending across its upper, marginal edge, except at both lateral sides. Further in this regard, the inner face of plate 16 includes a major planar surface 16b and a step portion; the latter comprised of a minor planar surface 16c and a sloped region 16d that bridges the minor planar surface 16c and the major planar surface 16b. The major planar surface 16b and the minor planar surface 16c are substantially parallel to one another and to surfaces 14a, 14b and 16a. As also seen in FIG. 2, separation medium 23 extends from the separation zone at least partially into the loading zone, i.e., above the junction between sloped region 16d and the beginning of minor planar surface 16c.

The geometry of sloped region 16d is not particularly critical, although it is preferred that region 16d be free of significant discontinuities in its surface. Thus, the sloped region 16d may meet the major and minor planar surfaces 16b and 16c at an angle (e.g., such that region 16d is substantially flat), or alternatively, region 16d joins surfaces 16b and 16c by way of a smooth curve at each end of 16d. In the specific embodiment of FIG. 2, the junction between the sloped region 16d and the major planar surface 16b is angled, and the junction between the sloped region 16d and the minor planar surface 16c is smoothly curved. Preferably, the curved junction between surface 16c and 16b is formed as a circular arc spanning 1 to 4 degrees, and preferably about 3 degrees. In another preferred embodiment, the length of sloped region 16d in the direction leading from the top to the bottom of the plates is preferably at least twice the depth of the recess in plate 16 (i.e., the distance between surfaces 16a and 16b as measured in the direction perpendicular to those surfaces). Additionally, each inner and outer face of plates 14, 16 may be beveled about the periphery so as not to present any sharp points or edges.

In an exemplary embodiment, the plate-to-plate distance between surfaces 14b and 16b is 0.2 millimeters and the plate-to-plate distance between surfaces 14b and 16c is 0.4 millimeters. However, other distances between surface 14b and surfaces 16b and 16c are also contemplated by the invention. In any case, the plate-to-plate distance separating surface 14b and surface 16b should be less than the plate-to-plate distance separating surface 14b and surface 16c. By this construction, a comb 24 (e.g., 0.4 millimeters face-to-face) that is thick relative to the thickness of most of the electrophoresis medium layer, can be accommodated in the gap between surface 14b and surface 16c. This is because most of the electrophoresis medium layer 23 resides in the much narrower gap (e.g., 0.2 millimeters) between surface 14b and surface 16b. Thus, most of the electrophoresis medium layer 23 is ultra-thin, while the comb 24 and the sample loading regions formed with the comb are comparatively thick.

As best seen in FIG. 1, the top edge of plate 16 is cut away across the width of the plate, except at both lateral ends. The resulting cutout provides access for a buffer solution to make contact with the top edge of the electrophoresis medium layer.

At this point it should be noted that the region between the plate surfaces 14b and 16b is referred to herein as the separation zone, and the region between the inner surfaces of the plates in the recessed region (i.e., between surface 14b and surface 16c) is referred to herein as the loading zone or reservoir. The region between the plate surfaces 14b and 16d, communicating the separation zone and the loading zone, is referred to herein as the tapered portion. Additionally, the distance between the confronting surfaces of the plates 14, 16 is referred to herein as the plate-to-plate distance. As previously discussed, the plate-to-plate distance in the separation zone should be less than the plate-to-plate distance in the loading zone.

The plates 14, 16 may be made using any suitable material. In a preferred embodiment, the plates are made of a flat, chemical resistant, borosilicate glass with a low thermal expansion, such as that sold under the trade name BOROFLOAT® or TEMPAX®. In this embodiment, both sides of each plate (14, 16) should be ground and polished to remove tin from the glass surface and to generate a high degree of flatness. Computer numerically controlled (CNC) machining may then form the shaped region of the plate 16. For example, a CNC rotary tool fitted with a silicon carbide grinding wheel may initiate grinding near one lateral edge of plate 16 and continue grinding while moving laterally across the plate to a position near the other lateral edge. In this fashion, the shaped region can be ground in a single, continuous step. Thus formed, the shaped region has substantially uniform dimensions throughout.

Figure 4:
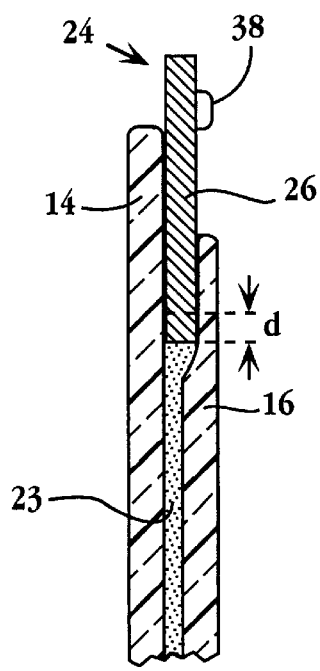
FIG. 4 is a side cross-sectional view taken along the line 4—4 of FIG. 3.
Figure 3:
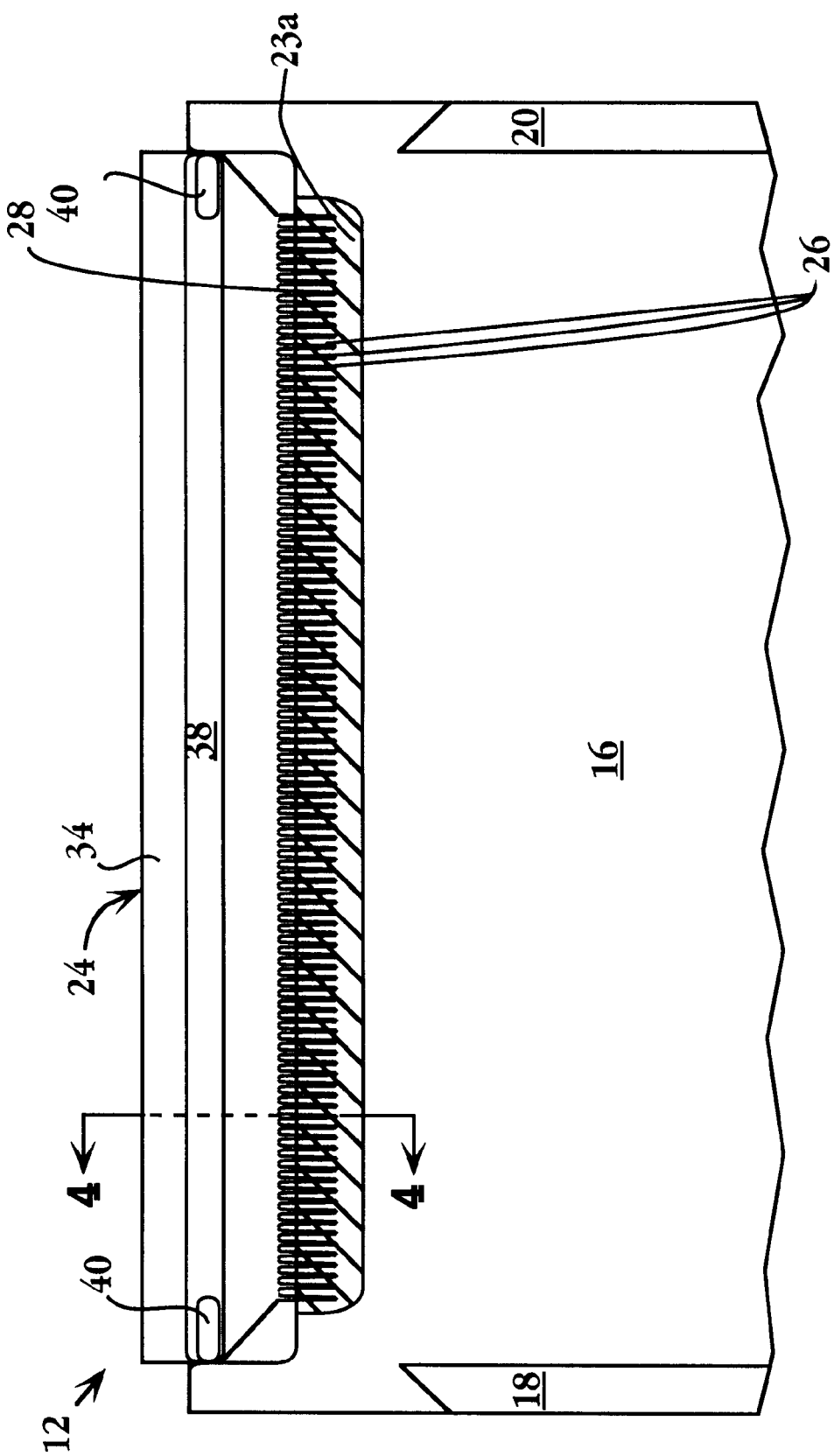
FIG. 3 is a front elevational view showing the slab gel electrophoresis apparatus of FIG. 1 with the comb inserted into the loading region between the confronting plates.

FIG. 3 is a front elevational view showing the comb 24 as it is set in the electrophoresis apparatus 12 of the invention. The teeth, as identified by the reference numeral 26, should fit snugly in the gap 22 between the plates 14, 16, within the loading zone, so that the spaces between adjacent pairs of teeth are isolated from one another so that sample leakage between wells is prevented. As best seen in the side, cross-sectional view of FIG. 4, the tips of the teeth are partly buried to a depth "d" in the electrophoresis medium layer 23. For typical sequencing gels, the depth "d" is preferably about 0.25 to 0.3 mm, to electrically isolate and form liquid-tight seals between adjacent sample spaces. When the teeth have substantially uniform thicknesses in the direction perpendicular to the plate surfaces, it is preferred that the tips of the teeth do not extend beyond the junction between surface 16c and sloped region 16d, to prevent possible deformation of the teeth due to increased tightness in sloped region 16d.

In this way, each tooth 26 serves as a wall that separates two adjacent spaces, such as 28 in FIG. 3, to be filled with a sample of interest. Such spaces 28 are referred to herein as loading regions. Preferably, there are at least 49 teeth extending off of the support member, and more preferably at least 97 teeth, to collectively provide at least 48 or 96 loading regions 28, respectively, with each preferably having substantially the shape of an inverted "U." The upper portion of each loading region 28 extends above the upper edge of the shaped plate 16 to provide access for a sample loading implement (not shown) so that a sample aliquot may be deposited proximate the gel surface 23a.

Figure 5:
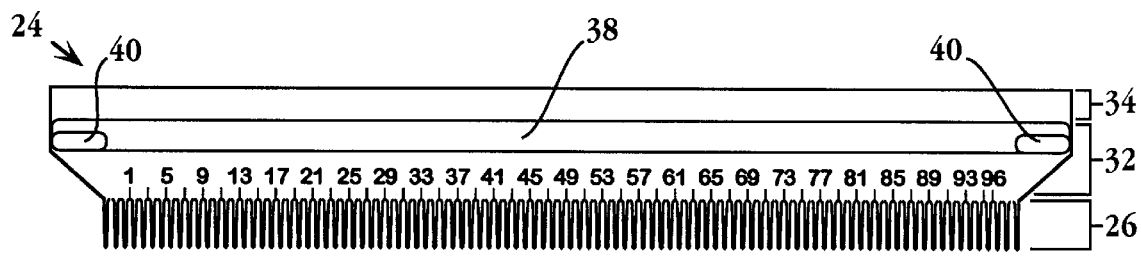
FIG. 5 is a front elevational view showing a comb according to an embodiment of the present invention.
Figure 6:
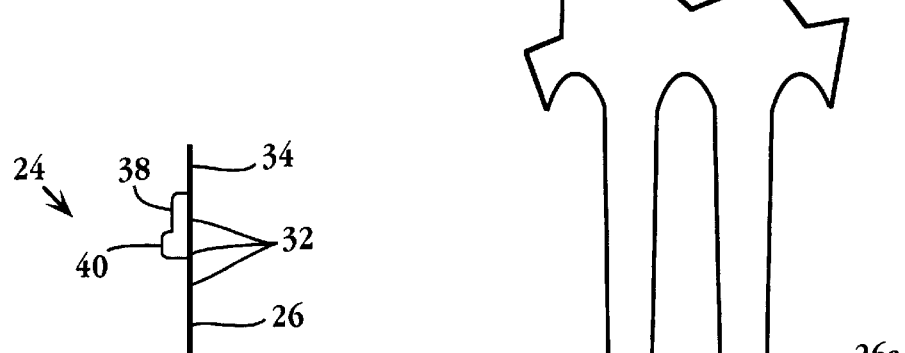
FIG. 6 is a side elevational view of the comb of FIG. 5.

The comb 24, as illustrated in the front and side elevational views of FIGS. 5 and 6, respectively, is optionally constructed of two components. One component is cut from a sheet of MYLAR® (DuPont), or another rigid, inert material, to include (i) an elongate, central support 32, (ii) a straight-edge 34 (optional) extending off of one lateral edge of the support 32, and (iii) a series of evenly spaced teeth 26 extending off of the other lateral edge of the support 32. The material from which this component is formed should be of uniform thickness throughout. In an exemplary embodiment, this component is 0.4 millimeters thick. The other component is an elongate, semi-rigid, stop-bar 38 made from polycarbonate, or the like, which is permanently bonded to, and fully extends across the length of, an upper portion of the support 32. The upper and lower edges of the stop-bar 38 are flat, as well as the face abutting the support 32. The stop-bar 38 should be substantially thicker than the support 32, the former preferably having a thickness of about 2 to 3 millimeters. By way of further illustration only, with reference to FIG. 5 and the exemplary dimensions just noted for the first comb component and stop-bar 38, the exemplary comb has a length of about 20 cm along its longest dimension, and a height (from the top of straight-edge 34 to the distal ends of the teeth) of about 3.1 cm. A pull-tab 40 may be formed at each end of the stop bar 38 to facilitate pulling the comb 24 out from between the plates 14, 16.

Next, the teeth 26 of the comb 24 will be described. Certain terms used herein in describing the dimensions of the teeth have the following intended meanings: "width" is co-extensive with the plane of the comb and perpendicular to the longitudinal axis of a tooth, and extends from one lateral edge of the tooth to the other lateral edge of the tooth; "length" extends from the interface whereat the tooth meets the lateral edge of the support to the extreme tip of the tooth, in a direction co-extensive with the longitudinal axis of the tooth; and, "thickness" or "depth" is co-extensive with a plane perpendicular to the plane of the comb and bisecting a tooth along the tooth's longitudinal axis, and extends from one lateral face of the tooth to the other lateral face of the tooth.

In general, the comb used in practicing the invention can have any configuration that achieves (i) a snug fit with the surfaces of the opposing plates and (ii) provides liquid-tight, electrically isolated sample loading regions between adjacent teeth of the comb. A number of comb designs are known in the art and need not be detailed here. Preferably, however, each tooth in the comb contains (i) a first portion beginning proximal to and extending away from the support member, such that the first region is optionally tapered, and (ii) a second, terminal portion that is more tapered than the first region and has a pointed end, for forming a liquid-tight seal with the top of the separation medium. In a more specific embodiment, each tooth has (i) a first tapered portion which tapers gradually beginning proximate to the support member and extending along most of the tooth's longitudinal axis, and (ii) a second tapered portion, more sharply tapered than the first tapered portion, which optionally begins immediately beyond the first tapered portion and extends along the tooth's longitudinal axis to an end of the tooth distal from the support member. Such features will now be discussed with reference to the particular configuration shown in FIG. 7.

Figure 7:
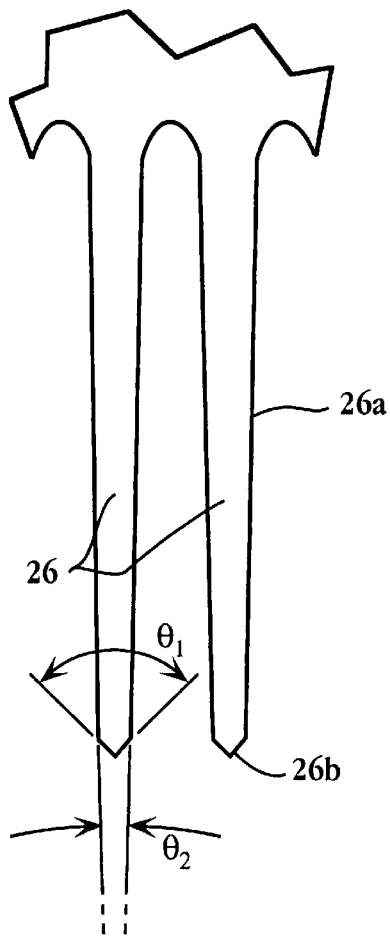
FIG. 7 is a partial, enlarged view showing two teeth of the comb of FIG. 5.

As seen in the enlarged view provided in FIG. 7, each tooth 26 has a gradually tapered portion 26a along most of the tooth's longitudinal axis. Here, the width of tooth 26 gradually decreases, and is thus tapered, in the direction away from the support 32. Preferably, respective lines defined by each edge of this first tapered portion, projected out in the direction away from the support member, converge at an angle $\theta_2$ of from 0 to 5 degrees. Each tooth 26 also has a second tapered portion 26b that is more sharply tapered than the first portion, along its longitudinal axis beyond the shallow taper. Here, the width of tooth 26 in portion 26b decreases in the same direction, but much more rapidly than in the tapered portion 26a. As shown in FIG. 7, the second, terminal tapered portion preferably ends with a terminal point at the vertex of angle $\theta_1$. Preferably, $\theta_1$ is from about 80 to about 100 degrees. Alternatively, instead of ending at a point, the terminal portion of each tooth 26 may be blunt or slightly rounded.

One advantage of having a relatively sharp tip at the end of each tooth, such as region 26b in FIG. 7, is that such sharp ends help form a liquid-tight, electrically isolated seal with the separation medium by penetrating slightly into the surface of the medium. In experiments conducted in support of the invention, the inventors have found that a good seal is significantly more difficult to achieve with blunt-ended teeth because they cannot adequately "grip" the surface of the medium so as to prevent sample cross-over between adjacent loading regions. Sharper ends, on the other hand (e.g., where $\theta_1 > 80$ degrees), are more susceptible to bending and can lead to tearing of the separation medium.

In the particular configuration shown in FIG. 7, the terminal tapered portions 26b begin immediately beyond the first portion 26a. However, the invention also contemplates embodiments in which regions 26a and 26b are separated by a third portion (not shown) having edges that are parallel or tapered, depending on design choice. Similarly, the edges in proximate portion 26a can be chosen to be parallel to each other, rather than tapered. Preferably, however, the edges of the teeth are tapered along their entire length in the longitudinal direction, at least to some degree, in order to impart greater rigidity to the teeth along their entire lengths, to prevent bending when the comb is inserted into the sample loading zone of the plates.

In a preferred embodiment, the teeth 26 are all of uniform thickness (in the direction perpendicular to the plate surfaces) and length. In an exemplary embodiment, the thickness of each tooth is about 0.4 millimeters or slightly greater (to ensure a snug fit with the plates), and the length of each tooth is about 10 millimeters. Further in this embodiment, the first, proximate tapered portion extends along the tooth's longitudinal axis a distance of about 9.7 millimeters from the support's lateral edge, and the second, more sharply tapered region 26b extends along the tooth's longitudinal axis for a distance of about 0.27 millimeters beyond the first tapered portion. Additionally, and for illustrative purposes only, the width at the transition of the shallow taper and sharp taper is about 0.54 millimeters.

As shown in FIG. 5, identifying means may be printed on the surface of the comb 24 to ensure that the user can clearly recognize where to inject samples. For example, numerals and/or ruled lines may be provided to indicate sample lanes 1–96. It should be appreciated that the great number of wells provided by the comb of the invention permits the loading of more samples for a single electrophoretic run than has previously been possible, which contributes to a higher throughput analysis.

Components which are not shown in the drawings are clamps used to hold the two plates together, a support structure for holding the plates in a vertical position, and electrode buffer reservoirs which contact the top and bottom edges of the gel. Such components, and their method of use, are well known in the art.

Conveniently, the apparatus of the invention can readily be retrofitted into existing equipment. It is contemplated that the apparatus of the invention should be particularly useful as a 96-lane upgrade for an ABI 377 Prism™ DNA Sequencer (Applied Biosystems Division of The Perkin-Elmer Corporation).

Another aspect of the invention provides a method for separating bio-organic molecules using a slab gel. Preferably, the method is practiced in connection with an electrophoresis apparatus as described above. The method is particularly useful for the electrophoretic separation of nucleic acids, such as DNA, using an ultra-thin gel.

In a preferred embodiment, the method is practiced with a slab gel electrophoresis apparatus having a pair of spaced, confronting plates defining a multi-lane separation zone adapted to hold a separation medium and an upper loading zone, and a comb having a plurality of teeth adapted to be inserted into the loading zone for holding samples and defining sample lanes. According to the method, the comb is inserted into the loading zone so that the teeth abut an upper portion of the separation medium, thereby forming a series of fluid-tight, elongate sample-loading apertures of substantially rectangular cross-section having a plate-to-plate width greater than that of the inter-plate distance in the separation zone.

With reference to the figures, the plates 14, 16 are placed face-to-face so that the shaped region of the plate 16 confronts the inner face 14b of plate 14. Spacers strips 18, 20 are interposed at both vertical edges to establish a gap 22 between the plates 14, 16. As previously discussed, the the gap 22, in turn, determines the width for the interposed gel 23. Thus, if it is desired to form an ultra-thin gel having a thickness of 0.2 mm within the separation zone, then 0.2 mm spacer strips should be employed. Once the spacer strips 18, 20 are in place, the plates 14, 16 are then compressed together by any suitable means (not shown), which could include any of various type of clamps or clips along their lateral edges.

A seal (not shown) is placed along the open top edge of the confronting plates 14, 16. In a preferred embodiment, the seal is provided by straight edge 34 of comb 24 (FIG. 5) which is dimensioned to leave small aperatures on either side of the comb, in order for air to escape during filling of the gel. In this regard, comb 24 is inverted (with the teeth 26 pointing away from the plates) and its straight edge 34 is pushed down between the plates 14, 16 before the gel solution is poured into the gap 22. The stop bar 38, being substantially wider than the gap 22 along the lower open edge of the plates 14, 16, ensures that the straight edge 34 extends down to the desired depth uniformly from one lateral side of the loading zone to the other lateral side. The straight edge 34 thus serves to establish both the straightness and height of the upper edge 23a of the gel 23.

A separation medium, such as a polyacrylamide gel solution, is prepared and poured into the lower open end of the plates, until the entire separation zone is filled. The medium is then allowed to solidify.

After the gel 23 has solidified, comb 24 is removed and inverted to the position shown in FIGS. 2 and 3 of the drawings. The tips of the teeth 26 should be pressed down into the gel so that they become partly buried to a depth "d" in the gel 23. Preferably, the depth "d" is about 0.25–0.3 mm. In this way, each tooth 26 serves as a wall that separates two adjacent spaces, or loading regions, such as 28, to be filled with a sample of interest. The upper portions of the loading regions 28 between the teeth 26 should extend above the upper edge of the shaped plate 16 to provide access for a sample loading implement so that sample aliquots may be deposited proximate the gel surface 23a. In FIG. 3, for example, about 70% of the length of the teeth extend into the loading zone of the plates, and the other 30% remains outside of the plates. This ensures adequate sample volumes (e.g., on the order of 1.5 microliters) in the loading zone while at the same time providing access for the tip of a micropipette to load the sample loading regions (sample wells). The tip of the micropipette is carefully lowered through the U-shaped region between adjacent teeth to just above the separation medium, and the sample is gradually released into the sample well while the micropipette is simultaneously withdrawn.

Next, the top and bottom of the polymerized gel are placed in electrical contact with respective buffer reservoirs (not shown). For the upper buffer reservoir, the inner, upper region of plate 14 and the comb 24 form one side wall, and the U-shaped spaces extending above the upper edge of the shaped plate 16 will be entirely immersed in the upper buffer solution.

Samples are loaded into the loading regions 28 along the upper edge of the gel 23. In this regard, the recessed region of plate 16 facilitates the depositing of samples into the loading regions 28 by permitting insertion of a sample-loader tip (not shown) having an outer diameter substantially greater than the inter-plate distance within the separation zone. In a preferred embodiment, the inter-plate width within the shaped region allows a loader tip of nearly 0.4 mm to be inserted between the plates 14, 16 for depositing samples proximate the gel surface. Conveniently, conventional pipettes can be used with the apparatus of the invention to load samples onto ultra-thin gels.

Subsequent to loading samples, an electric field is applied across the gel 23 and the samples are allowed sufficient time to migrate down the gel 23. As electrophoresis proceeds, the edge-to-edge width of each tooth 26, as measured at the gel surface 23a, establishes the dark space that will separate adjacent lanes corresponding to each sample. In this regard, since the present invention provides a greater tooth width at this interface than previous shark's tooth combs, the problem of insufficient dark space between adjacent lanes, often encountered with combs having very narrow teeth, is avoided.

At the end of the electrophoretic run, the plates 14, 16 are pried apart to expose the gel. The gel can then be dried and the results visualized, for example, by autoradiography.

In light of the description above and the accompanying drawings, it can be seen how the various objects of the invention are met. By providing an elongate recess in the sample loading zone of at least one of the two opposing electrophoresis plates, the present invention provides a way to increase the loadable volume of the samples while simultaneously facilitating the otherwise difficult loading of samples using conventional ultra-thin pipettes. further, by providing a loading zone with parallel opposing plate surfaces having a thickness greater than the separation medium, the plates of the invention promote a snug fit between the teeth of the comb and the plates, so that sample cross-over is effectively suppressed. The wider sample loading region also enables lanes to be placed more closely together since (i) narrowing of the lateral spacing between wells is offset by greater thickness of the wells in the direction perpendicular to the surfaces of the glass plates, and (ii) the increased thickness dimension lends increased rigidity to the teeth of the comb, so that narrower teeth can be used. Finally, by providing a comb embodiment wherein the spacing between edges of adjacent teeth at their distal end regions where the teeth cross the surface of the separation medium is a multiple less than 3 of the width of the individual teeth where the teeth cross the surface of the separation medium, the invention provides cleanly separated lanes with sufficient separation between lanes so that coalescence of sample bands from adjacent lanes is significantly avoided. Furthermore, the present invention dramatically increases the lane density that can be achieved in electrophoretic applications such as nucleic acid sequencing, by providing combs that afford lane densities of greater than about 5 lanes per centimeter, roughly doubling previous standard lane densities.

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

It is claimed:

1. In a slab gel electrophoresis apparatus having a pair of spaced, confronting plates defining a multi-lane separation zone adapted to hold a separation medium and an elongate upper loading zone, and a comb having a plurality of teeth adapted to be inserted into the loading zone to define therewith a plurality of loading regions that communicate with the separation zone, an improvement comprising:

an elongate recess formed in the upper portion of at least one plate, said recess forming, together with the confronting plate, an elongate upper loading zone having a plate-to-plate distance which (i) is substantially constant throughout said upper loading zone and (ii) is greater than the plate-to-plate distance within the separation zone;

an elongate tapered portion joining the separation zone with the loading zone, said elongate tapered portion having a plate-to-plate distance that progressively decreases from the loading zone to the separation zone; and a separation medium held between said confronting plates within said separation zone and extending at least partially into said tapered portion.

2. The slab gel electrophoresis apparatus of claim 1, wherein said separation medium extends from said separation zone at least partially into said loading zone.

3. The slab gel electrophoresis apparatus of claim 1, wherein said elongate recess extends across at least 70% of the lateral width of one of said plates.

4. The slab gel electrophoresis apparatus of claim 3, wherein the plate-to-plate distance within said separation zone is less than 0.3 mm, and wherein the plate-to-plate distance within said loading zone is greater than 0.3 mm.

5. The slab gel electrophoresis apparatus of claim 4, wherein the plate-to-plate distance within said separation zone is about 0.2 mm.

6. The slab gel electrophoresis apparatus of claim 3, wherein the plate-to-plate distance within said loading zone is from 1.5 to 3 times greater than the plate-to-plate distance within said separation zone.

7. The slab gel electrophoresis apparatus of claim 1, wherein said teeth extend off one edge of an elongate support member; and wherein each tooth has (i) a first tapered portion which tapers gradually beginning proximate to said support member and extends along at least half of the tooth's longitudinal axis, and (ii) a second tapered portion, more sharply tapered than said first tapered portion, which begins immediately beyond said first tapered portion and extends along the tooth's longitudinal axis to an end of the tooth distal from said support member.

8. The slab gel electrophoresis apparatus of claim 1, wherein said teeth extend off one edge of an elongate support member and are positioned between said confronting plates in said loading zone with their distal end regions penetrating a surface of said separation medium; and wherein the spacing between edges of adjacent teeth at their distal end regions where the teeth cross the surface of the separation medium is a multiple less than 3 of the width of the individual teeth where the teeth cross the surface of the separation medium.

9. In a slab gel electrophoresis apparatus having a pair of spaced, confronting plates defining a multi-lane separation zone adapted to hold a separation medium and an elongate upper loading zone, and a separation medium held within said separation zone; a comb comprising:

an elongate support member;

a series of teeth extending from one edge of said support member; wherein:

said teeth are positioned between said confronting plates in said loading zone with their distal end regions penetrating a surface of said separation medium;

said teeth and confronting plates define a plurality of loading regions, between adjacent teeth, that communicate with the separation zone;

the spacing between adjacent teeth at their distal end regions where the teeth cross the surface of the separation medium is a multiple less than 3 of the width of the individual teeth; and at least one of said plates has an elongate recess across an upper portion thereof, said recess forming, together with the confronting plate, an elongate upper loading zone having a plate-to-plate distance which (i) is substantially constant throughout said upper loading zone and (ii) is greater than the plate-to-plate distance within the separation zone; said plate further including an elongate tapered portion joining the separation zone with the loading zone, said elongate tapered portion having a plate-to-plate distance that progressively decreases from the loading zone to the separation zone; and wherein said separation medium extends at least partially into said tapered portion.

10. In a slab gel electrophoresis apparatus having a pair of spaced, confronting plates defining a multi-lane separation zone adapted to hold a separation medium and an elongate upper loading zone, and a separation medium held within said separation zone; an improvement comprising:

a comb having an elongate support member and a series of teeth extending from one edge of said support member;

wherein each tooth has (i) a first tapered portion which tapers gradually beginning proximate to said support member and extending along at least half of the tooth's longitudinal axis, and (ii) a second tapered portion, more sharply tapered than said first tapered portion, which begins immediately beyond said first tapered portion and extends along the tooth's longitudinal axis to an end of the tooth distal from said support member;

wherein said teeth are positioned between said plates in said loading zone with the distal end of each tooth penetrating said separation medium, thereby forming a plurality of elongate loading regions, between adjacent teeth, that communicate with the separation zone.

11. The apparatus of claim 10, wherein said teeth have front and rear surfaces that are substantially planar and parallel to one another.

12. The apparatus of claim 11, wherein said separation medium within said separation zone is less than 0.3 mm thick, and wherein said teeth of said comb are greater than 0.3 mm thick.

13. The apparatus of claim 12, wherein the face-to-face thickness of the comb is 1.5 to 3 times greater than the plate-to-plate distance within said separation zone.

14. The apparatus of claim 11, wherein at least 97 teeth extend off said edge of said support.

15. The apparatus of claim 11, wherein each loading region has substantially the shape of an inverted "U."

16. The apparatus of claim 10, wherein at least one of said plates has an elongate recess formed in the upper portion thereof, said recess forming, together with the confronting plate, an elongate upper loading zone having a plate-to-plate distance which (i) is substantially constant throughout said upper loading zone and (ii) is greater than the plate-to-plate distance within the separation zone; said plate further including an elongate tapered portion joining the separation zone with the loading zone, said elongate tapered portion having a plate-to-plate distance that progressively decreases from the loading zone to the separation zone; and wherein said separation medium extends at least partially into said tapered portion.

17. In a slab gel electrophoresis apparatus having a pair of spaced, confronting plates defining a multi-lane separation zone adapted to hold a separation medium and an elongate upper loading zone, and a separation medium held within said separation zone; a comb comprising:

an elongate support member;

a series of teeth extending from one edge of said support member;

wherein said teeth are positioned between said confronting plates in said loading zone with their distal end regions penetrating a surface of said separation medium;

wherein said teeth and confronting plates define a plurality of loading regions, between adjacent teeth, that communicate with the separation zone;

wherein said teeth have front and rear surfaces that are substantially planar and parallel to one another;

wherein the face-to-face thickness of the comb is a multiple greater than 1.1 of the plate-to-plate distance in the separation zone.

18. A method of preparing a slab gel electrophoresis apparatus for use in separating bio-organic molecules, comprising:

providing a pair of spaced, confronting plates defining a multi-lane separation zone and an upper loading zone, a separation medium held within said separation zone, and a comb having a plurality of teeth adapted to be inserted into the loading zone;

inserting said comb into said loading zone so that distal ends of said teeth penetrate an upper portion of said separation medium, thereby forming a plurality of loading regions, between adjacent teeth, that communicate with the separation zone;

wherein said loading regions are of substantially rectangular longitudinal cross-section, and wherein the plate-to-plate distance within said loading regions is greater than the plate-to-plate distance in the separation zone.

* * * * *